United States Patent [19]

Ogawa et al.

[11] Patent Number: 4,955,360
[45] Date of Patent: Sep. 11, 1990

[54] HEAT-GENERATING MATERIAL FOR PORTABLE HAIR CURLER

[75] Inventors: Yoshihiro Ogawa; Hiroo Takahashi; Yoshinori Kikuchi, all of Kamaishi, Japan

[73] Assignees: Nippon Steel Corporation; Finetec Co., Ltd., both of Tokyo, Japan

[21] Appl. No.: 316,965

[22] Filed: Feb. 28, 1989

Related U.S. Application Data

[63] Continuation-in-part of Ser. No. 179,221, Apr. 8, 1988, abandoned.

[30] Foreign Application Priority Data

Apr. 10, 1987 [JP] Japan ................................ 62-53478
Jul. 16, 1987 [JP] Japan ................................ 62-108285

[51] Int. Cl.$^5$ ............................................. F24J 1/00
[52] U.S. Cl. ............................... 126/263; 126/206; 126/269; 44/3.1; 132/227; 132/228
[58] Field of Search ................. 126/263, 206, 269; 44/3.1, 3.3, 3.6, 3.8; 132/227, 228

[56] References Cited

U.S. PATENT DOCUMENTS

| | | | |
|---|---|---|---|
| 3,228,403 | 1/1966 | Pasternack | 126/263 X |
| 4,205,957 | 6/1980 | Fujiwara | 126/263 X |
| 4,603,706 | 8/1986 | Caruso | 132/41 |

FOREIGN PATENT DOCUMENTS

| | | |
|---|---|---|
| 630347 | 5/1936 | Fed. Rep. of Germany . |
| 637457 | 10/1936 | Fed. Rep. of Germany . |
| 989551 | 9/1951 | France . |
| 51-76782 | 6/1976 | Japan . |
| 51-81183 | 6/1976 | Japan . |
| 53-47744 | 12/1978 | Japan . |
| 54-151585 | 10/1979 | Japan . |
| 56-145402 | 11/1981 | Japan . |
| 59-16501 | 2/1984 | Japan . |
| 60-94101 | 6/1985 | Japan . |

OTHER PUBLICATIONS

"Hair Curling Appliances" (JIS C 9616).
Japanese Industrial Standard (1977).
"Introduction to Chemical Engineering" HATTA (1966).
"Disposible Pocket Heater", Japan Disposible Pocket Trade Association (1989).
"Chemical and Education" Ishizuka 37, No. 1 (1989).
"The Defense Agency Technical Report" Technical Report No. 154 (1965).
"Disposable Body Warmers" (JIS 54100).
Japanese Industrial Standard (1985).

*Primary Examiner*—Larry Jones
*Attorney, Agent, or Firm*—Wenderoth, Lind & Ponack

[57] ABSTRACT

A metallic heat-generating agent comprising as a main component iron powder and water generating steam by an oxidation reaction caused by contact with air is contained in an air-permeable bag as a heat-generating material for a portable hair curler. A portable hair curler is constructed and operated by exchangeably inserting this metallic heat-generating material in a hair-winding guide cylinder and dismountably attaching a cover after winding the hair onto the hair-winding guide cylinder.

3 Claims, 9 Drawing Sheets

BEFORE USE → IN USE

Fig.9(b)

BEFORE USE → IN USE

HEAT-GENERATING MATERIAL FOR PORTABLE HAIR CURLER

This is CIP application of USSN 179,221 filed Apr. 8, 1988, now abandoned.

BACKGROUND OF THE INVENTION (1) Field of the Invention

The present invention relates to a heat-generating material for a portable hair curler, and to a hair curler using this heat-generating material.

More particularly, the present invention relates to a heat-generating material for a portable hair curler, which does not damage the hair during curling thereof and can be supplied at a low cost, is easily handled, rapidly curls the hair, and can be thrown away after use, and to a hair curler using this heat-generating material.

(2) Description of the Related Art

As is well-known, hair-curlers of the type utilizing the generation of heat by electricity are conventionally used, but, for structural reasons, hair curlers of this type are heavy and bulky, and are not easily portable.

With the recent development of pocket heaters utilizing a metallic heat-generating agent, various portable hair curlers (hot curlers) utilizing such a metallic heat-generating agent have been proposed. However, these hair curlers have the following disadvantages.

(1) For example, in a hair curler of the type where the hair is directly wound onto a metallic heat-generating material comprising a metallic heatgenerating agent contained in an air-permeable bag (see, for example, Japanese Unexamined Utility Model Publication No. 59-16501), an excessive heat-generating effect is given to the hair, and the hair is often damaged. Moreover, since the hair must be touched by the hands when curling, there is a fear that problems will arise due to a breakage of the metallic heat-generating material. Especially, since women users generally allow their nails to grow very long for reasons of fashion, the risk of a breakage of the metallic heat-generating material is very high.

(2) In a hair curler comprising a metallic heat-generating agent packed in a hollow cylinder onto which the hair is wound (see, for example, Japanese Unexamined Utility Model Publication No. 51-76782), since an element for fixing the hair is not included, generally the hair is not properly curled. Moreover, since the metallic heat-generating agent is packed in the cylinder, when the curler is to be used, it is difficult to promote the necessary oxidation for obtaining a heat-generating action by lightly shaking the metallic heat-generating material. Furthermore, since an element for fixing the hair is not included, the operation of winding the hair is cumbersome, and the curling operation cannot be performed rapidly or easily.

(3) A hair curler in which the above-mentioned disadvantages are eliminated was proposed, for example, in Japanese Unexamined Utility Model Publication No. 51-81183. This hair curler is provided with a hair-fixing element, and thus the cumbersome operation of winding the hair is eliminated. However, since the composition of the metallic heat-generating agent is not specifically disclosed, it is difficult to ascertain whether it is possible to impart a moisturizing effect to the hair.

The reason why the composition of the heat-generating agent for generating heat by oxidation, as utilized for a hair curler, is not specified, is considered to be that this technique still needs much improvement and an effective composition has not been formulated as yet. Moreover, this non-clarification of the details of the composition leads one to assume that it is impossible to curl the hair while applying steam to the hair to attain a moisturizing effect, when this composition is used.

As other related arts, there can be mentioned Japanese Unexamined Utility Model Publication No. 54-151585 entitled "Throwaway Self-Heat-Generating Hair Curler", Japanese Unexamined Utility Model Publication No. 56-145402 entitled "Throwaway Hair-Winding Curler", Japanese Unexamined Utility Model Publication No. 60-94101 entitled "Hair Curler", and Japanese Examined Patent Publication No. 53-47744 entitled "Steam Hair Iron".

As can be seen from these prior arts, hair curler technology is rapidly developing.

The hair curler proposed in Japanese Examined Patent Publication No. 53-47744 is one of the most popular in use at present, but for structural reasons, the hair curler is not easily portable or easily used. The hair curler proposed in Japanese Unexamined Utility Model Publication No. 60-94101 is disadvantageous in that the hair curler is not easily used and the cost is high, because butane gas or the like is used.

The self-heat-generating curlers disclosed in Japanese Unexamined Utility Model Publication No. 54-151585, Japanese Unexamined Utility Model Publication No. 59-16501, and Japanese Unexamined Utility Model Publication No. 56-145402 are improved versions of the above-mentioned hair curlers, in that they handle easily and cost less, and users are able to carry and use them as portable hair curlers. In these self-heat-generating hair curlers, since water is removed from the hair wound on a hair-curling member, on the contact side, to attain a curling effect (the hair is bent or coiled), an imbalance in the water content of the hair often occurs. Accordingly, these hair curlers are defective in that damage to the hair is repeated and worsened when the hair is curled many times successively and thus it is difficult to maintain the hair in a healthy state.

Accordingly, these conventional portable hair curlers (hot curlers) have not been marketed because of these defects. Further, even if marketed, safe transportation or use cannot be guaranteed, and a hair curler which satisfies all of the requirements of a rapid operation, ease of handling, and lasting curling and moisturizing effects, has not been developed.

SUMMARY OF THE INVENTION

Therefore, a primary object of the present invention is to overcome the defects of the conventional techniques and provide a metallic steam-heat generating material for a portable hair curler, which satisfies all of the above-mentioned requirements.

Another object of the present invention is to provide a portable hair curler comprising this heat-generating material, in which the defects of the conventional portable hair curlers are eliminated.

Namely, according to the present invention, there is provided a metallic heat-generating material for a portable hair curler, which exerts the following effects when used for a hair curler, and there is further provided a portable hair curler comprising this metallic heat-generating material.

(1) Safety is ensured during transportation or during use. For example, the generation of unnecessary heat and damage such as a breaking of the hair curler are prevented.

(2) Easily portable.

(3) The heat-generating material or hair curler is easy to handle.

(4) The price is very low (i.e., the price is such that the curler can be easily purchased).

(5) The metallic heat-generating material is disposable, i.e., throwaway type.

(6) Damage to the hair is minimized.

(7) A moisturizing effect is continuously given to the hair.

(8) The curling of the hair is completed within about 12 minutes.

(9) The metallic heat-generating materials are exchangeable.

More specifically, in accordance with the present invention, there is provided a heat-generating material for a portable hair curler, which comprises a steam-heat generating agent comprising iron powder, steam-heat generating water, a water-retaining agent for retaining the water and a halide, and an air-permeable bag containing the heat-generating agent therein. Furthermore, in accordance with the present invention, there is provided a hair curler containing this heat-generating material therein.

BRIEF DESCRIPTION OF THE DRAWINGS

FIG. 1 is a perspective view of a metallic heat-generating material for a portable hair curler according to the present invention;

FIG. 2 (a) is a perspective view of the pressing member of the entire structure of a portable hair curler comprising the metallic heat-generating material shown in FIG. 1;

FIG. 2 (b) is a perspective view of the winding member of the entire structure of a portable hair curler comprising the metallic heat-generating material shown in FIG. 1;

FIG. 3 is a front view of an example of a commercial product of the portable hair curler according to the present invention;

FIG. 9 (a) shows the variation of the state of use of the metallic heat-generating material according to the comparative example 1, and FIG. 9 (b) the variation of the state of use of the metallic heat-generating material according to the example 1;

FIG. 12(a) is a perspective view of the outer surface of a cover of the hair curler shown in FIG. 10; and, FIG. 12(b) is a perspective view of the inner surface of a cover of the hair curler shown in FIG. 10.

DESCRIPTION OF THE PREFERRED EMBODIMENTS

Note: Throughout the drawings, the same referential numerals represent the same members, as follows:

1, metallic heat-generating material; 2, air-permeable bag; 3, metallic heat-generating agent; 4, winding member; 5, hollow portion; 6, projection; 7, fine hole; 8, pressing member; 9, flange; 10, packaging bag (air-permeable); 11, portable hair curler; 12, hair-winding guide cylinder; 13, cap; 14, cover; 15, vent hole; 16, comb tooth-like projection; 17, clearance; 18, opening; 19, vent hole in cover; 20, projection; 21, air-tight bag or container.

Figures 1, 2A, 2B, 3:
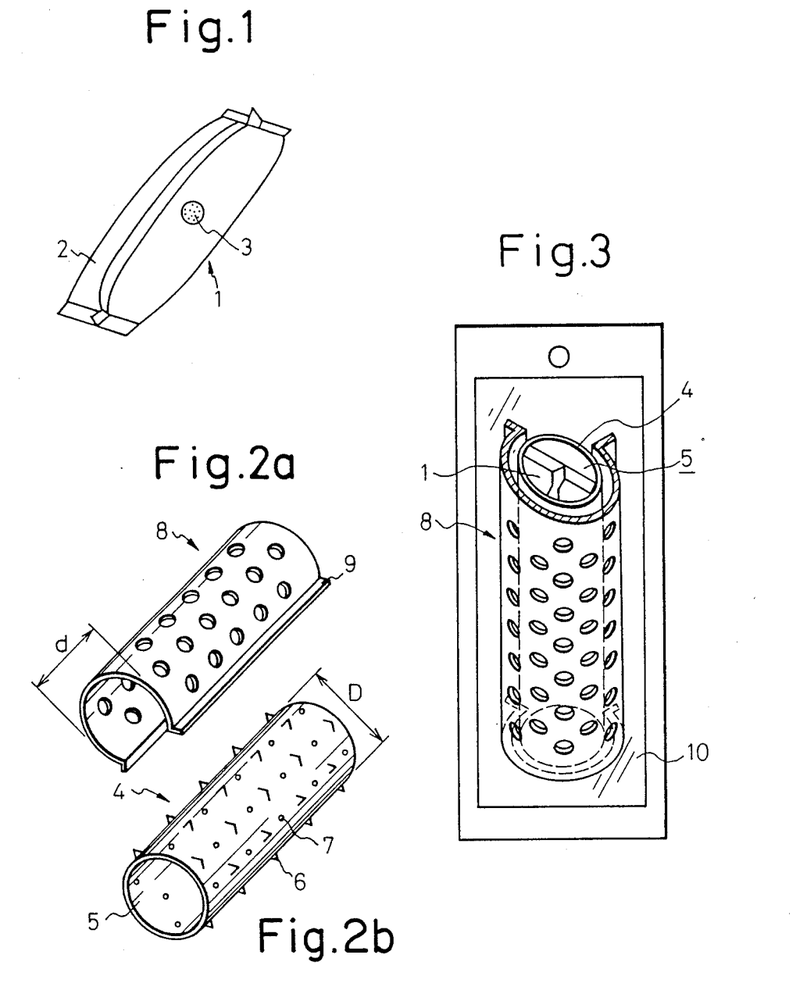

A metallic heat-generating material 1 for a portable hair curler according to one aspect of the present invention is shown in FIG. 1, wherein a part of the bag is cut away to illustrate the metallic heat-generating agent 3. Namely, this heat-generating material 1 comprises a metallic heat-generating agent 3, described in detail hereinafter, and an air-permeable bag 2 containing the metallic heat-generating agent 3 therein.

The bag 2 is composed of, for example, a nylon non-woven fabric/polyethylene laminate having vent holes or a polyethylene nonwoven fabric (marketed under the tradename of "TYVEK"), having a good air-permeability and contributing to the temperature-elevating action and steam dissipating action of the metallic heat-generating material.

The metallic heat-generating agent 3 used in the present invention must have the following composition:

Iron powder: 62.7±3%
Zeolite: 21.5±4%
NaCl: 3.1±2%
NaOH: 0.6±0.2%
Active carbon: 1.8±1.2%
Water: 10.3±3%
(Total 100%)

By using this hair curler, a physical phenomenon occurs in which heat is generated in a short time not obtainable by the conventional technique, i.e., about 2 to 3 minutes, a temperature of 90° to 100° C. is maintained for a time necessary for the hair curling, i.e., for about 6 to 8 minutes, and then the temperature is abruptly lowered to about 40° to 50° C. in about 1 to 2 minutes, whereby a user becomes aware that the hair curling process is completed. In this physical phenomenon, the total time required from the start of the process to the arrival at the above-mentioned completion temperature is about 10 to 12 minutes. Accordingly, the technical idea of the metal heat generator of the present invention is very different from the technical idea of the metal heat generator of the conventional portable hair curler characterized in that heat is gradually generated with an elapse of time and the required temperature is maintained for a required time.

Furthermore, according to the present invention, as the oxidation or hydration reaction is advanced, water is vaporized as steam and projected (diffused) outside the air-permeable bag, and therefore, a moisturizing effect is obtained.

The reasons for the limitation of the composition in the metal heat generator of the present invention will now be described.

The reason for limitation of iron powder content to 62.7±3.0 is now described.

The reason for limitation of iron powder content to 62.7±3.0% is now described.

In the metal heat generator of the portable hair curler of the present invention, the iron powder is a substance to be oxidized, and the content (%) of the iron powder should be such that the temperature of 90° to 100° C. necessary for the hair curling process is generated in a predetermined time of 2 to 3 minutes and is maintained for 6 to 8 minutes.

Since an object of the present invention is to firmly curl not only long hairs but also short hairs, the content (%) of the iron powder is important.

Furthermore, another object of the present invention is to satisfy the user's desire to accomplish the hair curling by a portable hair curler within a short time such as about 10±2 minutes.

Accordingly, the iron powder should be incorporated in a minimum amount necessary for generating the heat needed for the curling process in such a way that a highest temperature of 90° to 100° C. is maintained for 6 to 8 minutes and the temperature is then lowered promptly to about 40° to 50° C. in about 1 to 2 minutes.

Furthermore, another of the objects of the present invention is to impart a moisturizing effect to the hair and give a required curl to the hair without damaging same.

In view of the foregoing, in the present invention, the lower limit of the iron content is 62.7−3.0%. This lower limit indicates a state wherein the iron powder content is high and the substance to be oxidized is excessively incorporated. In connection with the iron powder content, preferably a salt is incorporated as the adjustor of rate of oxidation in a minimum necessary amount, together with water in a theoretically necessary amount and a water-retaining agent in an amount necessary for retaining this water. However, the value of the lower limit differs according to the grade of the iron powder. If the amount incorporated of the iron powder is smaller than 62.7−3.0%, the substance to be oxidized or the like is not wastefully lost, but to elevate the temperature to 80° C. in 2 to 3 minutes, a certain area of iron powder is necessary, and therefore, the iron powder content is increased, when an iron powder having an usual particle size construction is used. However, if the iron powder content is unnecessarily reduced, the apparent density is lowered and the bulk is increased, and the intended objects cannot be obtained.

On the other hand, if the iron content exceeds the upper limit of 62.7+3.0%, the iron powder amount is excessive and the apparent heat for heating the non-used iron powder to 90° to 100° C. is wastefully consumed. Where the curling is to be carried out at a relatively low temperature over a long period as in the metal heat generator of the conventional portable hair curler, the increase of the heat capacity of the entire heat generator by increasing the iron powder content is effective. But, even in this case, in the heat generator having a small capacity for a hair curler, the upper limit of the iron powder content specified in the present invention is 62.7+3.0%.

A reduced iron powder of the hematite type ore is preferred as the iron powder. Mill scale, a reduced iron powder of the magnetite type ore, an atomized iron powder and a pulverized iron powder have a specific surface area smaller than 400 cm$^2$/g and generally do not give the required effects.

The reason for the limitation of the content of zeolite (e.g., marketed under the tradename "ZEOPHYL") to 21.5±4.0% is now described. The zeolite acts as a water-retaining agent for retaining the water necessary for oxidation (hydration) of the iron powder and 90% of the incorporated water is retained in the zeolite. Accordingly, the zeolite mixing ratio is determined according to the theoretically necessary amount of water.

The lower limit of the zeolite mixing ratio is restricted to 21.5−4.0% because if the mixing ratio of zeolite is lower then this lower limit, the amount of water retained by the unit amount of zeolite is increased, the starting material becomes wet, and the proportion of water dissipated in the form of steam is increased. The upper limit of the mixing ratio is restricted to 21.5+4.0% because, if the zeolite mixing ratio exceeds this upper limit, the amount of water retained by the unit weight of zeolite is reduced, the apparent density is reduced (to no purpose), and the heat-generating agent becomes bulky, which degrades the bag-preparing property.

The reason for the limitation of the halide (e.g., sodium chloride (NaCl)) mixing ratio to 3.1±2.0% is now described. In the metallic heat-generating material of the present invention, NaCl acts as a catalyst for promoting the oxidation of the iron powder. The present inventors studied the heat-generating characteristics necessary for a metallic heat-generating material for a hair curler and found that the elevation time required for the temperature to rise to 90° C. is preferably 2 to 3 minutes and the maximum temperature is preferably 90° to 100° C. If the NaCl mixing ratio is lower than 3.1−2.0%, the elevation time is too long, i.e., 5 to 10 minutes, and if the NaCl mixing ratio exceeds 3.1+2.0%, the starting material becomes very wet and viscous. Therefore, the NaCl mixing ratio is limited to 3.1±2.0%.

The reason for the limitation of the agent for controlling the generation of hydrogen (e.g., sodium hydroxide (NaOH)) mixing ratio to 0.6±0.2% is now described. The NaOH controls the generation of hydrogen gas when the iron powder is oxidized (hydrated) by the metal halide.

If the NaOH mixing ratio is lower than 0.6−0.2%, hydrogen gas is generated, and when a pure iron powder is used, this generation of hydrogen gas is conspicuous. Even if NaOH is added in an amount exceeding 0.6+0.2%, the NaOH effect is not particularly increased, the elevation time as a heat-generating characteristic is prolonged, and the alkalinity of the heat-generating agent is increased. Preferably, the mixing ratio of NaOH is 0.6±0.2%.

The mixing ratio of active carbon is limited to 1.8+1.2%, because, in the metallic heat-generating agent of the present invention, active carbon adsorbs the water-retaining agent and oxygen in the atmosphere. Namely, when heat is generated by the heat-generating material, the active carbon supplies the water necessary for oxidation, and oxygen from the atmosphere is introduced into the bag containing the metallic heat-generating agent by the active carbon to ensure a smooth heat-generating reaction.

If the active carbon mixing ratio is lower than 1.8−1.2%, a sufficient amount of oxygen is not supplied to the heat-generating agent and heat generation of the oxygen passage-determined rate in the package occurs. Accordingly, the lower limit of the active carbon mixing ratio is restricted to 1.8−1.2%. If the active carbon mixing ratio exceeds 1.8+1.2%, heat generation of the iron powder at the oxidation-determined rate occurs and the intended effect cannot be realized. Accordingly, the upper limit of the mixing ratio of active carbon is restricted to 1.8+1.2%.

The reason for the limitation of the water mixing ratio to 10.3±3.0% is now described.

The water in the iron powder type metal heat generator acts as an oxidant of the iron, as outlined by the following chemical formula:

The amount of water necessary for the heat generator of the present invention can be theoretically calculated, but if it is intended, as in the portable hair curler of the present invention, to obtain a high temperature of 90° to 100° C. in a short time of about 2 to 3 minutes and to maintain this high temperature of 90° to 100° for 6 to 8 minutes, the content of the iron powder must be increased, for the above-mentioned reasons. Accordingly, if water is incorporated in an amount proportional to this iron content, the maintenance of the high temperature is prolonged, and the intended objects cannot be obtained. Accordingly, in the present invention, in view of the heat-generating characteristics, the amount of water incorporated is adjusted to a level lower than 35% of the theoretically necessary amount of water. In the present invention, water is incorporated in an amount smaller than the theoretically necessary amount, although a generation of steam is still expected. The reduction of the amount of water incorporated to 25 to 45% of the theoretically necessary amount of water is based on a novel concept that the temperature characteristic of the portable hair curler of the present invention or the time of the duration of the high temperature is adjusted by the amount of water incorporation.

If water is incorporated in this amount, after 6 to 8 minutes from the time at which the high temperature is reached by a generation of heat by the metal heat generator, the incorporated water is consumed by a hydration reaction of the iron powder and diffused outside the system in the form of steam due to a vaporization of the water, with the result that the hydration reaction of the iron powder is abruptly stopped and the temperature is abruptly lowered.

It has been found that, even if water is incorporated in the metal heat generator in an amount smaller than the theoretically necessary amount, water is diffused in the form of steam from the heat generator. The diffusion time is short, but in the present invention, the time required for the hair curling should be 6 to 8 minutes, and practical problems do not arise even if the diffusion time is short. Since it has been confirmed that, even if the amount of water is as small as 25% of the theoretically necessary amount of water, steam is generated, the lower limit of the amount of water is set at 10.3−3.0%.

The reason why the upper limit of the amount of water is set at 10.3+3.0% is that, if water is added in an amount exceeding this upper limit, the starting material becomes sticky and the intended heat-generating characteristics cannot be obtained. Accordingly, the amount of water incorporated is preferably 10.3±3.0%.

Water is incorporated in an air-permeable bag according to the following embodiments.
(a) Water is incorporated into the zeolite.
(b) Water is mainly incorporated in active carbon.
(c) Water is contained in the same bag together with the metal heat-generating composition but separately therefrom.
(d) Saw dust is incorporated and water is included in the saw dust.
(e) The above-mentioned water-retaining agent is used in combination with water.

An appropriate embodiment is selected from among these embodiments.

The reason for a limitation of the air permeability (JIS P-8117) of the bag for the metal heat generator to 60 to 1000 seconds is now described.

One of the technical problems of the present invention is to elevate the temperature to the application level of 90° to 100° C. in 2 to 3 minutes, and to accomplish this, it is necessary to oxidize the metal heat generator at a highest possible speed. In principle, preferably the permeability of the bag for the metal heat generator is highest.

The reason for limiting the air permeability to at least 60 seconds is as follows. If the air permeability is lower than 60 seconds, during the short period of time from the point of packing of the metal heat generator into the air-permeable bag to the point of filling this bag into the barrier vessel, i.e., during the period of 30 seconds, the oxidation of the metal heat generator is advanced and the variation of the temperature characteristics becomes large. Furthermore, if the air permeability is smaller than 60 seconds, steam is released without resistance and an expected inflation of the bag by the inner pressure of steam cannot be obtained. Accordingly, the heat transfer capacity between the inner surface of the hair-winding guide cylinder and the outer surface of the metal heat generator-containing bag is reduced, and the intended objects cannot be obtained.

The reason for setting the upper limit of the air permeability to 1000 seconds is as follows. As the air permeability is low, the oxidation of the metal heat generator is advanced at the speed controlled by the air permeability, the temperature characteristics become dull, and the duration is prolonged, and the time required for the curling operation is lengthened and becomes longer than 15 minutes.

If the air permeability is thus limited, the total time required for the hair curling can be adjusted to 10 to 12 minutes, regardless of whether the hair is long or short. This means that the temperature is elevated to the highest level of 90° to 100° C. necessary for the hair curling in 2 to 3 minutes, this temperature of 90° to 100° C. is maintained for 6 to 8 minutes, and then the temperature is promptly lowered to 50° to 40° C. in 1 to 2 minutes to make the user aware that the curling operation is completed.

This phenomenon is not observed in conventional hair curlers but only in the hair curler of the present invention. From the experience of applicant's company, which manufactures and sells large quantities (about 2,000,000 per month) of portable hair curlers, it has been found that users desire to curl hair in a short time (within 12 minutes) without damaging the hair and regardless of the length of the hair. The hair curler of the present invention has been developed as a means of satisfying this desire, and accordingly, the present invention provides an unprecedented novel metal heat generator for a hair curler.

As shown in FIG. 1, when the metallic heat-generating material 1 having the above-mentioned structure is used, the bag 2 is lightly shaken to mix the metallic heat-generating agent 3 and produce a reaction therein, and the bag 2 is then inserted in the hollow portion of the winding member 4.

Subsequent to the above process, as shown in FIG. 2(a) and FIG. 2(b) the hair is wound on the winding member 4 and the pressing member 8 is fitted thereover. Since the hair is gripped between the winding member 4 and the pressing member 8, the hair will remain in the set position until these members 4 and 8 are separated. Namely, since the outer diameter D of the winding member 4 is nearly equal to the inner diameter d of the pressing member 8 (D=d), movement of the hair is prevented.

If projections 6 are formed on the winding member 4, an appropriate clearance is formed in the wound hair during the winding of the hair, and an effective curling of the hair obtained.

As shown in FIG. 2(a) and FIG. 2(b) many fine holes are formed in the winding member 4 to allow a smooth dissipation of the steam, and thus obtain a continuous moisturizing effect. Namely, steam dissipated from the metallic heat-generating material 1 passes through the fine holes 7 and is impinged on the hair, whereby the steam, together with the elevated temperature (90° to 100° C.), causes the hair to curl while maintaining a good water balance in the hair. The time required for this curling operation is about 10 to 12 minutes.

When the winding member 4 is to be removed from the hair, the flange 9 is expanded and the pressing member 8 is lifted off of the winding member 4. After completion of the curling operation, the metallic heat-generating material 1 is removed from the hollow portion 5 and thrown away, the pressing member 8 is fitted to the winding member 4 and these members are stored in this state until required for use again. If the members 4 and 8 are composed of a consumable material, they can be thrown away together with the metallic heat-generating material.

FIG. 3 shows an example of a metallic heat-generating material 1 which is now commercially available. A packaging bag 10 is composed of a gas-barrier packaging material (for example, a vinylidene chloride-coated polypropylene or nylon/polyethylene laminate) or an aluminum foil/polyethylene laminate (aluminum foil packaging material). Accordingly, the metallic heat-generating material 1 is safely stored so that a reaction can not occur before use. Since the metallic heat-generating material 1 is inserted into the hollow portion 5 of the winding member 4 and the pressing member 8 is fitted thereto, during transportation the metallic heat-generating material 1 is easily handled and a high safely is guaranteed. Score lines are formed in the packaging bag 10 so that one heat-generating material or a group of heat-generating materials can be separately handled, and accordingly, an appropriate number of metallic heat-generating materials may be separated according to the intended use.

Moreover, the packaging bag 10 can be formed as one bag, and accordingly, an appropriate form can be chosen for the packaging bag 10 to be marketed, so long as the metallic heat-generating material 1 is contained in the bag 10 in the state wherein the metallic heat-generating material 1 is inserted into the hollow portion 5 of the winding member and the pressing member 8 is fitted to the winding member, and the intrusion of oxygen is prevented.

Another example of the metallic heat-generating material 1 will be now described. In this example, one metallic heat-generating material 1 is contained in a gas-barrier bag.

When this heat-generating material is used, the gas-barrier bag is opened just before use, and the metallic heat-generating material 1 is taken out and filled into a hair-winding guide cylinder of a hair curler to be used. Namely, a metallic heat-generating material for filling is provided. Several metallic heat-generating materials for filling can be connectedly packaged in such a manner that they can be easily separated from one another.

Figure 10:
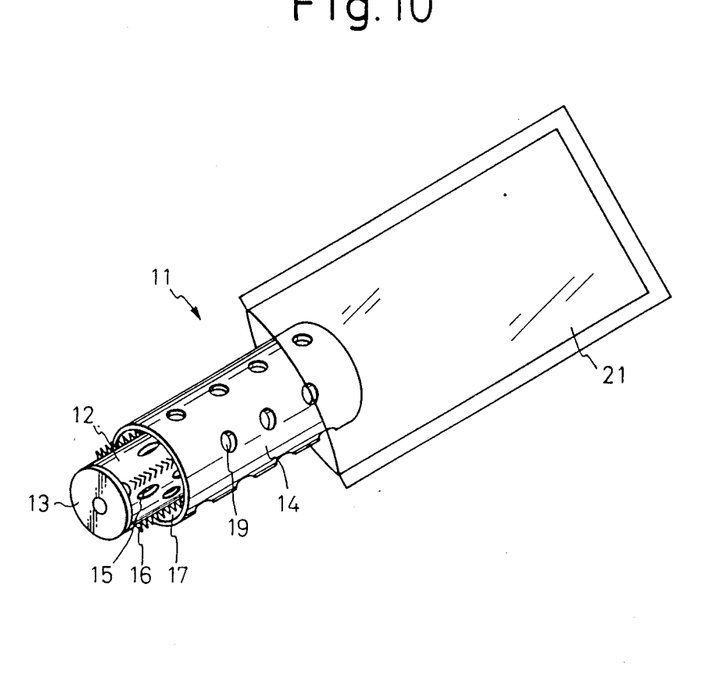
FIG. 10 is a perspective view of another example of a commercial product of the portable hair curler according to the present invention.

FIG. 10 shows another embodiment of the portable hair curler according to the present invention.

Referring to FIG. 10, a portable hot curler 11 comprises a hair-winding guide cylinder 12, a cap 13, and a cover 14. The metallic heat-generating material 1 shown in FIG. 1 is inserted into the hair-winding guide cylinder 12. Members other than the metallic heat-generating agent 3 of the metallic heat-generating material 1 are composed of a synthetic resin.

As shown in FIG. 3, the hair-winding guide cylinder 12 has a hollow cylindrical shape with vent holes 15 formed therein. Projections 16 resembling comb teeth, which extend in the longitudinal direction of the hair-winding guide cylinder 12, are formed at intervals on the outer surface of the cylinder 12 in the embodiment shown in FIG. 11. Six rows of projections 16 are arranged in this embodiment. When the hair-winding guide cylinder 12 is fitted to the cover 14, as explained hereinafter, the projections 16 resembling comb teeth prevent rotation of the hair-winding guide cylinder 12 and thus stabilize the winding of the hair. A clearance 17 is formed between the hair and the guide cylinder 12 so that the heat-generating action of the metallic heat-generating material 1 is appropriately exerted on the hair, and a continuous moisturizing effect by steam from the metallic heat-generating material 1 is easily obtained.

Figure 11:
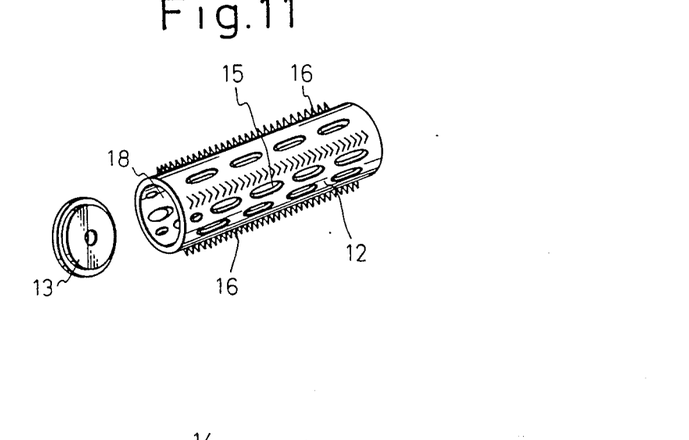
FIG. 11 is a detailed perspective view of a hair-winding guide cylinder of the hair curler shown in FIG. 10.

In the hair-winding guide cylinder 12, one end is closed in advance in the preparation process and an opening 18 is formed in the other end so that the metallic heat-generating member 1 can be exchangeably inserted therein. A cap 13 is fitted to that end to close the opening 18. Accordingly, the metallic heat-generating material 1 inserted in the hair-winding guide cylinder 12 can not fall out of the hair-winding guide cylinder 12 unless the cap 13 is removed. Accordingly, an unnecessary generation of heat can be prevented during transportation or use, and a high safety can be maintained. Note, a modification may be adopted in which both ends of the hair-winding guide cylinder 12 are open and caps are fitted to both openings to close the hair-winding guide cylinder 12.

Figures 12A, 12B:
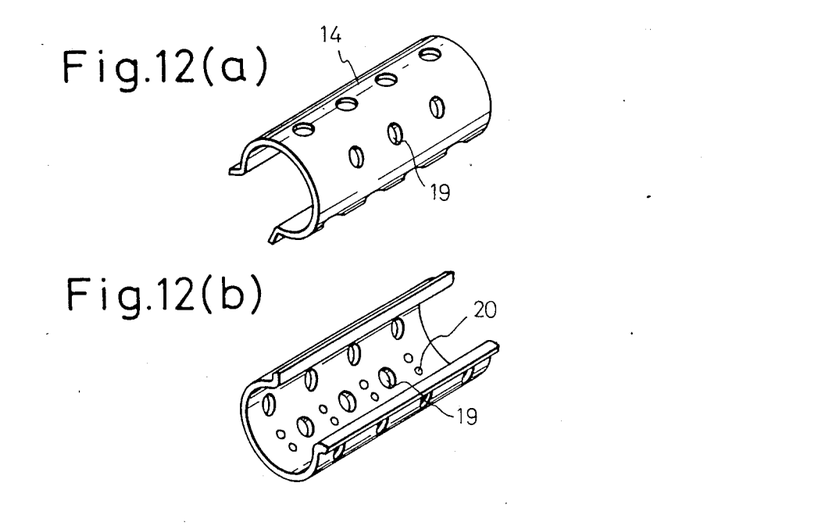

As shown in FIGS. 12(a) and 12(b), the cover 14 has vent holes 19 and four pairs of confronting projections 20 are arranged in the longitudinal direction on the inner wall of the cover 14. The projections 20 press against the above-mentioned projections 16 to prevent rotation of the hair-winding guide cylinder 12. The sectional shape of the cover 14 resembles the electric ohm symbol $\Omega$, and elasticity is imparted by this $\Omega$-like sectional shape. Accordingly, the hair-winding guide cylinder 12 can be turned by hand while fitted to the cover 14, and thus a good fitting state is maintained between the cover 14 and the hair-winding guide cylinder 12.

Furthermore, if the cover 14 is fitted to the hair-winding guide cylinder 12 as shown in FIG. 10, even when the cylinder 12 moves in the longitudinal direction of the cover 14, the hair-winding guide cylinder 12 will not separate from the cover 14 as it is held by the mutual action of the Ω-like sectional shape and the projections 16 formed on the hair-winding guide cylinder 12, unless released by hand, and therefore, a high safety can be maintained.

Before application, the metallic heat-generating material of the present invention is contained in a container vessel 21 such as an air-tight bag to prevent an unnecessary generation of heat, as shown in FIG. 10, and the metallic heat-generating material is marketed in this state.

At the time of application, the portable hair curler according to the present invention is removed from the bag 21, and the metallic heat-generating material 1 is lightly shaken to mix same. Then the hair is wound onto the hair-winding guide cylinder 12 containing the metallic heat-generating material 1, with air passing through from the vent holes 15 and 19, and the cover 14 is then fitted to the hair-winding guide cylinder 12. The temperature rapidly rises to about 90° to about 100° C., and the hair is curled. In this case, if water is contained in the composition of the metallic heat-generating material, this water is evaporated to impart a continuous moisturizing effect to the hair, and the hair is thus curled as desired.

The present invention will now be described in detail with reference to the following examples, that by no means limit the scope of the invention.

Note, these examples are directed to the metal heat generator for a thin type portable hair curler which can curl short hair as well as long hair, rather than only for users having short hair.

EXAMPLE 1

This example illustrates a metal heat generator 1 capable of curling short hair within a total required time of 10 minutes while imparting a moisturizing effect to the hair. Since a hematite type iron ore was used as the iron powder, the above-mentioned technical problems were solved. And accordingly, this metal heat generator had excellent characteristics.

Figure 4:
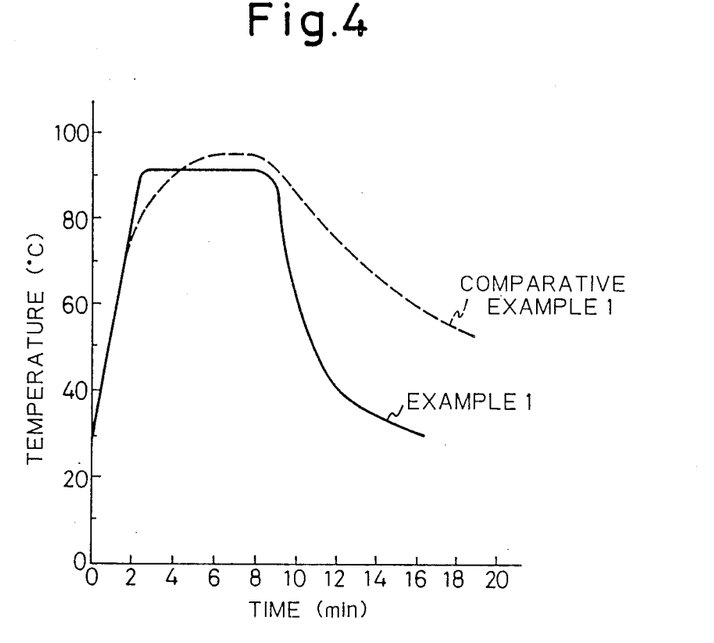
FIG. 4 shows the temperature-elevation curves of the metallic heat-generating material according to the present invention and of a comparative metallic heat-generating material.
Figure 5:
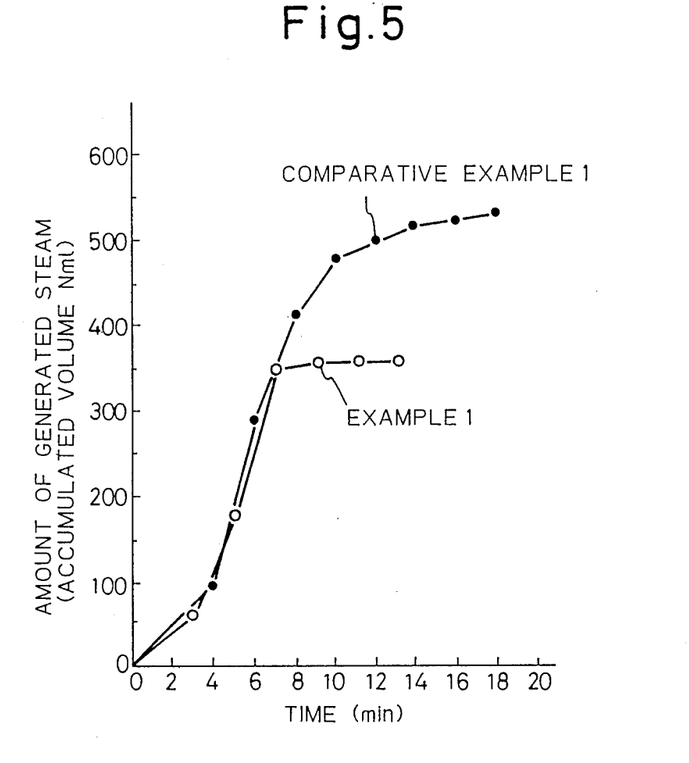
FIG. 5 shows the amount of water dissipated by the metallic heat-generating material according to the present invention and by the comparative metallic heat-generating material shown in FIG. 4.

FIGS. 4 and 5 are graphs showing the heat-generating curves and steam diffusion quantities of the metal heat generator 1 of the present invention and the metal heat generator of Comparative Example 1, respectively. As is apparent from these results, when the metal heat generator of the present invention was used, curls given a moisturizing effect were obtained in about 10 minutes.

Figure 9A:
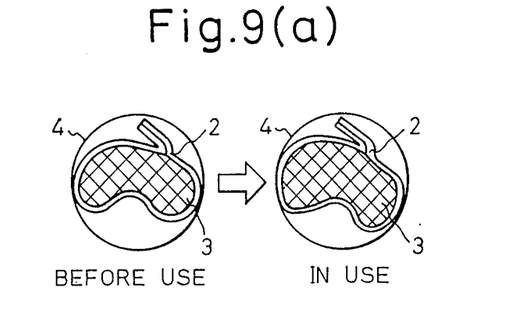

FIG. 9(a) shows the state where the metal heat generator of Comparative Example 1 is actually used. A vacant space is formed between the metal heat generator and a winding tool 4, as shown in FIG. 9(a). Accordingly, heat generated by the metal heat generator 1 is not sufficiently transferred to the winding tool 4 because of this vacant space, and therefore, the temperature of 90° to 100° C. necessary for the hair curling cannot be obtained promptly and stably.

Figure 9B:
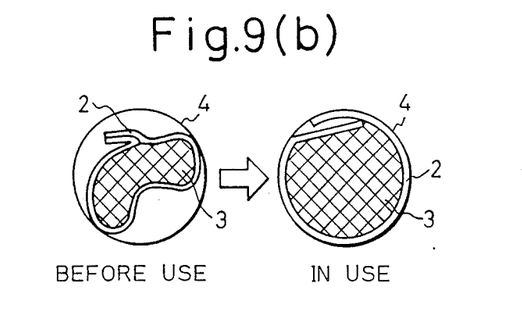

FIG. 9(b) shows the state where the metal heat generator 1 of the present invention is actually used. Since the metal heat generator 1 is inflated to the inner wall of the winding tool 4 with no vacant space therebetween, heat generated by the metal heat generator 1 is totally transferred to the winding tool 4 and is totally transferred to the wound hairs through fine pores 7. Accordingly, a heat-generation action necessary for curling short hair can be obtained, and short hair can be curled as well as long hair. Therefore, the limitations and conditions specified in the present invention are significant.

Composition of Metal Heat Generator for Present Invention

| Substance to be oxidized, iron powder | 62.7% |
|---|---|
| Water-retaining material, zeolite | 21.5% |
| Salts | |
| sodium chloride (NaCl) | 3.1% |
| caustic soda (NaOH) | 0.6% |
| Active carbon | 1.8% |
| Water | 10.3% |
| Total | 100.0% |

Method of Incorporation of Water

Water was contained in a zeolite (marketed under the tradename of "Zeofil") and mixing was carried out in advance.

Air-Permeable Bag 2

| (Air-Permeable Bag 2) | |
|---|---|
| Material: | laminate of non-wove fabric of polypropylene and polyethylene (porous) |
| Size: | |
| Thickness of material: | 90μ |
| Size of bag: | diameter d = 20 mm, length l = 80 mm (inclusive of end portions, each having length of 5 mm) |
| Air permeability: | 107 seconds |
| (Winding member 4 and Pressing member 8) | |
| Size: | |
| Winding member 4: | diameter D of periphery = 18 mm, length L = 60 mm |
| Pressing member 8: | inner diameter D' = 18 mm, length L = 60 mm |

COMPARATIVE EXAMPLE 1

The test was carried out in the same manner as described in Example 1 except that the composition of the metal heat generator was changed as indicated below.

| Substance to be oxidized, iron powder | 66.0% |
|---|---|
| Water-retaining material, zeolite | 19.6% |
| Salts | |
| sodium chloride (NaCl) | 2.9% |
| caustic soda (NaOH) | 0.5% |
| Active carbon | 1.6% |
| Water | 9.4% |
| Total | 100.0% |

EXAMPLE 2

This example illustrates the technical significances of the numerical limitations specified in the present invention. The present example is directed to the metal heat generator 1 capable of curling hair in a short time while imparting a moisturizing effect. In the comparative example, the composition was below the lower limit of the range specified in the present invention.

The lower limit referred to herein is the lower limit of the amount of iron powder incorporated and having the greatest influence on the metal heat generator of the present invention.

Accordingly, the mixing ratios of the respective components constituting the oxidation improver were relatively increased.

Figure 6:
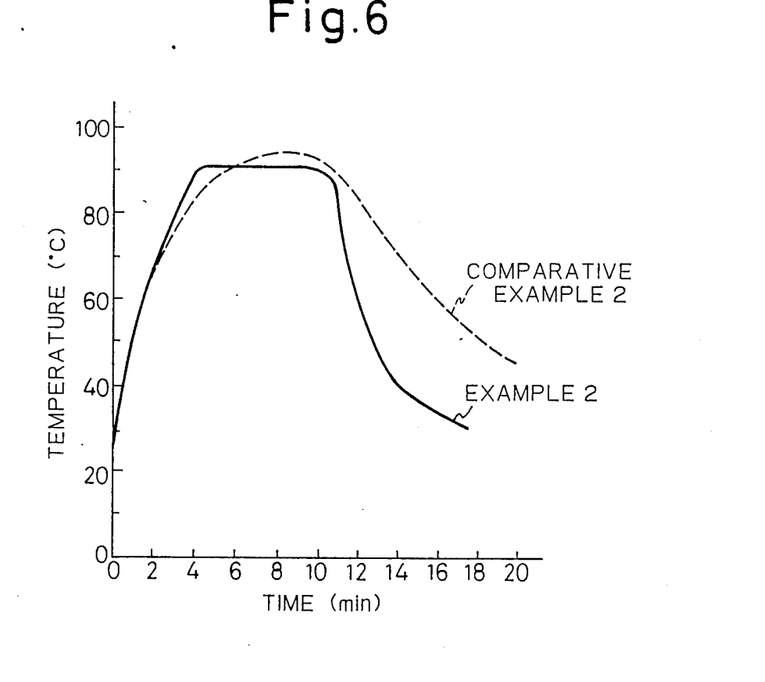
FIG. 6 shows the temperature-elevation curves of the metallic heat-generating material according to the present invention (example 2) and of a comparative metallic heat-generating material (comparative example 2)

As is seen from the graph shown in FIG. 6, the total time required for the hair curling was longer by 2 minutes than in Example 1 and the hair curling was completed in a total of 12 minutes. In Comparative Example 1, the total required time was prolonged and exceeded 20 minutes. It was confirmed that the metal heat generator of Comparative Example 1 could not solve the technical problems of the present invention and could not be practically used.

Composition of Metal Heat Generator of Present Invention

| Substance to be oxidized, iron powder | 60.0% |
|---|---|
| Water-retaining material, zeolite | 23.1% |
| Salts | |
| sodium chloride (NaCl) | 3.3% |
| caustic soda (NaOH) | 0.7% |
| Active carbon | 1.9% |
| Water | 11.0% |
| Total | 100.0% |

Method of Incorporation of Water

Water was contained in the zeolite and the water-incorporated zeolite was mixed with other components, and the mixture was filled in the air-permeable bag 2. To prevent an unnecessary reaction, the bag was promptly contained in a barrier bag to cut the contact with the open air.

Air-Permeable Bag

| (Air-Permeable Bag 2) | |
|---|---|
| Material: | laminate of polyethylene non-woven fabric and polyethylene (porous) |
| Size: | |
| Thickness of material: | 75μ |
| Size of bag: | end portion = 5 mm, diameter d = 20 mm, length l = 75 mm |
| Air Permeability: | 894 seconds |

Winding member 4 and Pressing member 8

The same conditions as described in Example 1 were adopted.

COMPARATIVE EXAMPLE 2

The test was carried out in the same manner as described in Example 2 except that the composition of the metal heat generator was changed as indicated below.

| Substance to be oxidized, iron powder | 58.0% |
|---|---|
| Water-retaining material, zeolite | 24.2% |
| Salts | |
| sodium chloride (NaCl) | 3.5% |
| caustic soda (NaOH) | 0.6% |
| Active carbon | 2.2% |
| Water | 11.6% |
| Total | 100.0% |

The upper limit referred to herein represents the upper limit of the amount of iron powder incorporated, which has an influence on the temperature characteristics of the metal heat generator of the present invention.

Accordingly, where the metal heat generator having this upper limit is used, the incorporation ratios of the respective components constituting the oxidation improver are relatively reduced.

EXAMPLE 3

Figure 7:
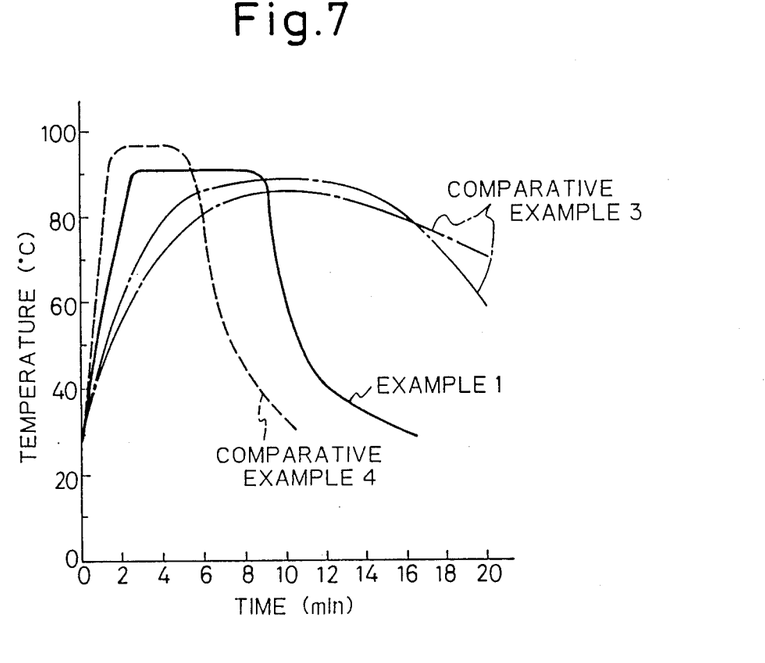
FIG. 7 shows the temperature-elevation curves of the metallic heat-generating material according to the present invention (example 1) and of a comparative metallic heat-generating material (comparative examples 3 and 4)

To confirm the technical significance of the air permeability condition of the bag among the conditions specified in the present invention, the test was carried out in the same manner as described in Example 1 except that the air permeability of the bag was changed. The results are shown in the graph of FIG. 7.

Note, the air permeabilities of the bag adopted in Comparative Examples 3 and 4 were as shown below.

Comparative Example 3: 1308 seconds and 1024 seconds.

Comparative Example 4: 46 seconds. As apparent from FIG. 7, the bag 2 of the present invention had a good air permeability and the heat-generating time of the metal heat generator was adjusted based on the air permeability of the bag 2.

Therefore, in the present invention, an optimum reaction speed of the metal heat generator 1 was obtained by appropriately combining the air permeability of the bag 2 with the composition of the metal heat generator 1.

EXAMPLE 4

This example illustrates the curling characteristics of various heat metal generators.

Sample No. 1 is a heat generator of the present invention having the following metal heat generator composition.

| Substance to be oxidized, iron powder | 62.5% |
|---|---|
| Water-retaining material, zeolite | 21.7% |
| Salts | |
| sodium chloride (NaCl) | 3.2% |
| caustic soda (NaOH) | 0.5% |
| Active carbon | 1.8% |
| Water | 10.3% |
| Total | 100.0% |

Sample No. 2 is a comparative sample having the same composition as that of sample No. 1 except that the content of the iron powder was changed to 66.5% and the water content was changed to 6.3%. Sample No. 3 is a comparative sample comprising 43.8% of the iron powder, 39.8% of the zeolite, and 16.3% of water and sample No. 4 is a comparative sample comprising 55.6% of the iron powder, 16.2% of charcoal (substitute for the zeolite) and 22.7% of water. Sample No. 5 is a comparative sample having the same composition as that of sample No. 3 but differing from sample No. 3 in the air permeability of the bag. Sample No. 6 is a comparative sample having a composition included within the scope of the present invention but having an air permeability of the bag exceeding the upper limit specified in the present invention.

Figure 8:
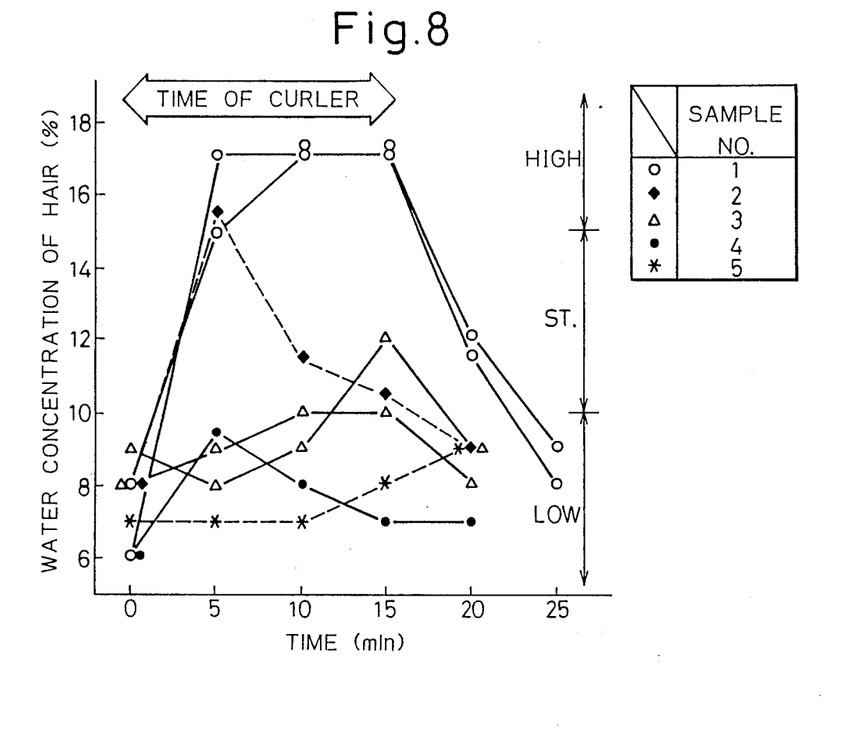
FIG. 8 shows the concentration of water for hair dissipated by the metallic heat-generating material according to the example 4.

FIG. 8 illustrates the relationship between the time elapsed after the curling and the water concentration (%) of the hair in the central portions thereof in the length direction, which was observed when the hair was curled by using sample Nos. 1 through 5. In the case of sample No. 1 of the present invention, after 5 minutes had passed from the completion of the curling, the water concentration in the hair was 17% and this concentration was maintained for about 10 minutes. In sample No. 2, the water concentration was as high as in sample No. 1 just after the curling, but the water concentration was drastically reduced because of the shortage of contained water. In sample Nos. 3 through 5, no substantial increase of the water concentration was observed. Accordingly, it is seen that no substantial moisturizing effect was attained in any of the comparative samples.

The curling characteristics (moisture effects) of these samples are shown in Table 1. In the case of sample No. 1, when the hair was set at 2 turns and then released, a curl finish of 1.3 turns was obtained, but in the case of sample Nos. 2 and 3, only curl finishes of 0.9 turn and 0.7 turn, respectively were obtained. In the case of sample Nos. 4 through 6, no curling effect was obtained.

The results shown in Table 1 demonstrate that the predetermined temperature and steam amount are necessary for obtaining a desired curl finish.

minutes and the generation of steam is stopped during this period).

(3) The hair curler is easy to carry.
(4) The hair curler is easy to handle.
(5) The price is low.
(6) The metal heat generator causing an autogenous generation of heat can be thrown away.
(7) Unnecessary heat is not applied to the hair in the dry state, and therefore, the hair is not damaged.
(8) A moisturizing effect can be given to the hair.

What is claimed:

1. A heat generator for a portable hair curler, which comprises (1) a heat-generating agent comprising 62.7±3.0% of an iron powder, 0.6±0.2% of NaOH, 21.5±4.0% of zeolite, 1.8±1.2% of an active carbon, 3.1±2.0% of NaCl, and 10.3±3.0% of water, the total amount being 100.0%, and (2) a bag for containing said heat-generating agent, which bag has vent pores for diffusing steam generated from the heat-generating agent to the outside to bring the hair into contact with said steam, and which bag has an air permeability of 60 to 1000 seconds as determined according to JIS P-8117.

2. A heat generator as set forth in claim 1, which is contained in an air-impermeable vessel.

3. A heat generator as set forth in claim 2, wherein a hair-winding member and a hair-pressing member are further contained in the air-impermeable vessel.

TABLE 1

| Sample No. | Characteristic of Sample | | | State of Generation of Heat | | | Curling Characteristics | | | Remarks |
|---|---|---|---|---|---|---|---|---|---|---|
| | Highest temperature (°C.) | Time(min) of retention of temperature of 90 to 100° C. | Water content (g/%) | Inflation of inner bag | Generation of steam (naked eye observation) | Amount (g) of Steam Generated from Heat Generator | Air permeability (seconds) (JIS P-8817) of Bag | Finish state | Durability (relative value) of curls | Increase of water concentration (%) in hairs | |
| 1 | 97.4 | 8.0 | 1.13/ 10.3 | observed | observed | 0.99 | 121–176 | *1 1.3/2.0 | 100 (16hr) | >10 | present invention |
| 2 | 98.7 | 6.3 | 0.75/ 6.8 | observed | observed (only in initial stage) | 0.52 | 121–176 | 0.9/2.0 | 70 | 7 (Maximum) | comparison |
| 3 | 81.6 | — | 1.19/ 10.8 | not observed | not observed | 0.43 | 280–362 | 0.7/2.0 | 60 | 3–4 (maximum) | comparison |
| 4 | 71.0 | — | 2.49/ 22.6 | not observed | not observed | 0.32 | 58–96 | bad | — | 3–4 (maximum) | comparison |
| 5 | 61.3 | — | 1.19/ 10.8 | not observed | not observed | 0. | 373–401 | bad | — | 1–2 (maximum) | comparison |
| 6 | 46.9 | — | 1.13/ 10.3 | not observed | not observed | 0. | 1056–1760 | bad | — | 0 | comparison |

Note
*1 1.3/2.0 indicates that curling finish of 1.3 turns was obtained when the hair was set at 2 turns and then released.

As is apparent from the foregoing description, if the metal heat generator for a hair curler according to the present invention is used, the following effects can be obtained.

(1) Short hair and long hair can be firmly curled.
(2) The termination of the hair curling can be detected by the relatively abrupt reduction of the heat generation temperature (the temperature of 90° to 100° C. is lowered to 50° to 40° C. in 1 to 2